United States Patent [19]

Morad et al.

[11] Patent Number: 4,894,376
[45] Date of Patent: Jan. 16, 1990

[54] METHODS OF TREATING DISEASES CHARACTERIZED BY HYPEREXCITABILITY OF NEURONS

[75] Inventors: Martin Morad, Newtown Square; Cha-Min Tang, Overbrook Hills, both of Pa.

[73] Assignee: Trustees of the University of Pennsylvania, Philadelphia, Pa.

[21] Appl. No.: 160,835

[22] Filed: Feb. 26, 1988

[51] Int. Cl.$^4$ .................. A61K 31/495; C07D 241/20
[52] U.S. Cl. .................................... 514/255; 544/407
[58] Field of Search ......................... 514/255; 544/407

[56] References Cited

U.S. PATENT DOCUMENTS 3,240,780  3/1956  Cragoe et al. ...................... 544/382
3,527,758  9/1970  Cragoe et al. ...................... 544/382

OTHER PUBLICATIONS

D. R. Bielefeld, et al., "3',4'-Dichlorobenzamil Inhibits Ca ad K Currents in Single Frog Atrial Cells", Circulation vol. 74, Abstract No. 686, 1986.
M. L. Garcia, et al.,. "Interaction of Amiloride Derivatives with the Cardiac Ca$^2$ + Entry Blocker Receptor Complex", Biophysical Journal 51: 428a (1987).
Takehiko Amano, et al., "Neurotransmitter Synthesis by Neuroblastoma Clones", Proc. Nat. Acad. Sci USA 69: No. 1 258-263 (1972).
A. Pousti, et al.,. "Effect of Amiloride on Isolated Guinea-Pig Atrium", Arch. Int. Pharmacodyn. 242: 222-229 (1979).
Shuji Yamashita, et al.,. "Cardiac Effects of Amiloride in the Dog", Journal of Cardiovascular Pharmacology 3: 704-715 (1981).
Hamill, et al., "Improved Patch-Clamp Techniques for High-Resolution Current Recording from Cells and Cell-Free Membrane Patches", Pflugers Arch 391: 85-100 (1981).
Barde et al., "Sensory Neurons in Culture: Changing Requirements for Survival Factors During Embryonic Development", Proc. Natl. Acad. Sci USA, vol. 77: 1199-1203.
Tang, et al., "Amiloride Selectively Blocks the Low Threshold (T) Calcium Channel", Biophysical Journal, vol. 53 (1988).
Richard T. Johnson, Excerpt from Current Therapy in Neurologic Disease-2, (1987), pp. 45-47.
Miller et al., "Are Dihydropyridine Binding Sites Voltage Sensitive Calcium Channels?", Minireview, Life Sciences, vol. 34:1205-1221 (1984).

Primary Examiner—Cecilia Shen
Attorney, Agent, or Firm—Woodcock Washburn Kurtz Mackiewicz & Norris

[57] ABSTRACT

The invention provides methods of treating diseases characterized by hyperexcitability of neurons. An amount of a substituted pyrazinoylguanidine compound effective to regulate excitability of the neurons is administered. Substituted pyrazinoylguanidines having the formula

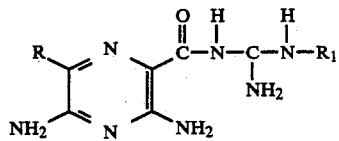

wherein R is halogen and R$^1$ is a member of the group consisting of hydrogen, benzyl and optionally substituted benzyl are useful in the invention. The invention also discloses a method of treating neurons having hyperexcitable cell membranes.

58 Claims, 5 Drawing Sheets

METHODS OF TREATING DISEASES CHARACTERIZED BY HYPEREXCITABILITY OF NEURONS

REFERENCE TO GOVERNMENT GRANT

The invention described herein was supported by National Institutes of Health grant R01-HL-16152 and NINCDS grant 1-K08-NS-01104. The government has certain rights in the invention.

BACKGROUND OF THE INVENTION

Electrically excitable cells are the building blocks of the nervous system and the cardiovascular system. Electrical excitability is the basis for the generation of rapid signalling between cells and the signal processing properties of the cells of the nervous system. It is also the basis for initiating the contraction of the muscle of the heart and the vascular smooth muscle that controls blood pressure. Electrical excitability arises from the ability of ions (i.e., sodium, potassium, and calcium) to rapidly move across channels bridging the inside and the outside of the cell. Because ions are electrically charged, the rapid movements of ions generate electric currents. The regulation of the conductances of these channels determines the electrical excitability of the cell. There are a number of different ionic channels in each cell. Each channel has its own distinct characteristics and plays distinct roles. Together they operate as an ensemble that serves to control the electrical behavior of the cell.

In living cells, an electrical potential exists between the inside and outside of the cell. This potential difference is called the membrane potential. At-rest electric potential on the inside of a typical cell is 60 to 80 millivolts more negative than the outside. Living cells also maintain the ionic composition of the cytoplasm to be different from that of the extracellular fluid. The concentration gradients for the ions between the inside and outside of the cell create the driving forces for the flow of ions through ionic channels. Calcium and sodium ions are maintained at very low concentration inside the cell compared to the outside. The reverse is true for potassium ions. If the calcium conducting channels (calcium channels) bridging the inside and outside of the cell are to open, there will be a rapid influx of calcium ion into the cell. The same is true for sodium and the sodium channel.

On the other hand, if the potassium channel is to open, potassium ions will rapidly flow out of the cell. Because these cations carry electric charges, the flux of ions generate an electric current. This current, in turn, controls the electrical potential difference between the inside and the outside of the cell (the membrane potential). When either the sodium or the calcium channel opens, cations enter the cell. This influx of positive charges causes the membrane potential to become more positive relative to its normal, resting membrane potential and the cell "depolarizes" or approaches the point at which it has no electrical charge. On the other hand, opening of the potassium channel leads to cations leaving the cell and a more negative membrane potential.

In order for neurons to generate an action potential and avoid the ionic gradient from rapidly running down, the ionic channel conductances are carefully controlled. The conductances of these channels are in turn tightly controlled by the membrane potential. At the resting membrane potential, most ion channels are closed. But if the membrane potential is depolarized to a certain point, the channel will open. The sodium channel, for example, will open when the membrane potential is depolarized to its threshold potential of −40 millivolts. The resulting influx of positively charged sodium ions leads to further membrane depolarization and further sodium channels openings. This regenerative depolarization results in the "action potential." The action potential is the basic signal within the nervous system. After opening, the sodium channels close rapidly. In the meantime, the slower responding potassium channels open in response to the membrane depolarization and bring the cell back to its resting membrane potential. The calcium channel is similar to the sodium channel in its ability to contribute to membrane depolarization, since opening of the calcium channels will result in a net influx of positively charged calcium ions.

Different types of channels have different biophysical properties. This heterogeneity of channel behavior permits differing physiologic roles for these channels. There are at least two types of voltage dependent calcium channels, the T and the L channel. They can be distinguished based on their voltage range of activation and their inactivation kinetic characteristics. The L type channel requires full membrane depolarization before activation, whereas the T type channels require only weak depolarization for activation. The T channel is activated at membrane potentials which are close to the resting membrane potential and near the membrane potentials for sodium channel activation. Besides contributing to neuronal excitability, calcium influx into neurons via ion channels is central to man aspects of neuronal function and dysfunction. These roles include control of neurotransmitter release, and regulation of calcium dependent intracellular enzymatic processes and second messenger roles. Excess calcium influx has also been shown to lead to neuronal death.

Pharmacologic agents that preferentially inhibit movement of calcium ions through voltage activated calcium channels are called calcium channel blockers. Three calcium channel blockers are presently approved for clinical use in the United States, nifidepine, verapamil, and diltiazem. These calcium channel blockers are highly potent in blocking the calcium channels in vascular smooth muscle and cardiac muscle. They are approved for use in treating angina, hypertension, and cardiac arrhythmia. They have also been effective in preventing coronary and cerebral vasospasm, and for use in treating migraine headaches. These calcium channel blockers, however, are much less effective on the calcium channels of neurons and also cause unacceptable side effects such as oversedation due to depression of neuronal function. Consequently, calcium channel blockers which are more effective in the nervous system are needed to treat a number of neurologic disorders that have already shown some responsiveness to the presently available calcium channel blockers. Furthermore, available calcium channel blockers lack selectivity for the different types of neuronal calcium channels. Nifidepine blocks only the L type calcium channel which predominates in the heart. Verapamil and diltiazem block both the L and T type calcium channels, but have less potency when studied in neurons. Thus calcium channel blockers which can selectively suppress the T type calcium channel without suppressing the L type channel ar needed to minimize the unwanted side effects that result from suppression of the L type channel when available calcium channel blockers are used to treat neurologic disorders.

Epilepsy is one neurologic disorder which has shown responsiveness to available calcium channel blockers. The clinical usefulness of these compounds, however, has been limited by unacceptable side effects, the most significant of which is oversedation. The exact cellular mechanisms causing epilepsy have not been clearly established, however, it has been shown that calcium channels mediate one of the major intrinsic mechanisms for generating the abnormal hyperexcitable behavior of neurons at the seizure focus. Recently, the prototypic anticonvulsant, diphenylhydantoin, has been shown to possess the property of suppressing the T type calcium channel. This may well be the mechanism for diphenylhydantoin,s well established anticonvulsant properties.

The pharmacologic treatment of painful neuropathies and central pain syndromes has employed many of the same compounds used in treating epilepsy including diphenylhydantoin. Both conditions are manifested by hyperexcitable neuronal behavior. Because of the role of the T type calcium channel in contributing to near threshold membrane excitability, selective suppression of the T channel will decrease neuronal hyperexcitability and raise the threshold for the perception of pain. Thus, there is a long-felt need for calcium channel blocking compositions which are selective for the T type calcium channel.

SUMMARY OF THE INVENTION

This invention is directed to methods of treating diseases characterized by hyperexcitability of neurons comprising administering an amount of a substituted pyrazinoylguanidine effective to regulate excitability of the neurons. It is believed that neurological diseases which can be characterized by hyperexcitability of neurons such as epilepsy, painful neuropathies and central pain syndromes will respond to treatment with the substituted pyrazinoylguanidine compounds useful in the invention.

The invention is further directed to methods of treating neurons having hyperexcitable cell membranes comprising administering an amount of a substituted pyrazinoylguanidine effective to regulate excitability of the neurons.

The invention is still further directed to methods of selectively suppressing the T type calcium channel in neurons comprising administering to the neurons a substituted pyrazinoylguanidine in an amount sufficient to effect said suppression.

The invention is also directed to the use of the compounds suitable for use in the invention in medicaments for treating diseases charterized byh hyperexcitability of neurons.

Substituted pyrazinoylguanidines having the structural formula wherein said R is halogen; and $R_1$ is hydrogen, $C_1$–$C_4$ alkyl, benzyl or substituted benzyl are believed to be useful in the practice of the invention.

It is believed that the substituted pyrazinoylguanidines useful in the invention preferentially suppress influx of calcium ions through the T type calcium channel. Diseases characterized by disturbances of excitability of neurons including diseases such as epilepsy, certain neuropathies, essential tremor, tachycardia, seizures, hypermotilities (e.g. gastrointestinal disorders), various psychiatric disorders such as manic depressive illness, and central pain (i.e. pain that is not local) are expected to respond the treatments of the invention.

The substituted pyrazinoylguandines useful in the invention are further believed to suppress the influx of calcium ions into the cell without suppressing the cell's ability to generate action potentials or suppressing the ability to activate the prototypic L type calcium channel, thereby allowing the cell to regain or maintain its normal functioning.

DETAILED DESCRIPTION OF THE INVENTION

Pyrazinoylguanidines having the formula wherein said R is halogen; and $R_1$ is hydrogen, $C_1$–$C_4$ alkyl, benzyl or substituted benzyl are suitable for use in the invention. R is preferably chlorine, iodine or bromine. Benzyl substituents can be any substituents that do not detract from the calcium blocking activity of the compound such as alkoxy, alkyl, and halogen. A preferred benzyl substituent is 3,4-dimethoxy. $C_1$–$C_4$ alkyl can be any group that does not detract from the calcium blocking activity of the compound. Bulky groups are believed to contribute to the calcium blocking properties of the compounds and are thus to be preferred for use in the invention. Substitution of hydrogen for the amino group at position 5 on the ring of amiloride causes loss of activity. Substitution of hydrogen at position 6 on the ring of amiloride causes a great decrease in activity.

Preferred substituted pyrazinoylguanidines include amiloride wherein R is chlorine and $R_1$ is hydrogen; benzamil wherein R is chlorine and $R_1$ is benzyl; 3,4-dimethoxybenzamil wherein R is chlorine and $R_1$ is 3,4-dimethoxybenzyl; 6-bromoamiloride wherein R is bromine and $R_1$ is hydrogen; and 6-iodoamiloride wherein R is iodine and $R_1$ is hydrogen.

The substituted pyrazinoylguanidines suitable for use in the invention can be synthesized generally in accordance with the methods of U.S. Pat. No. 3,527,758 "Process for the Preparation of Pyrazinoylguanidines From a Pyrazinoic Azide and a Guanidine", issued 9/8/1970 to Cragoe et al., which is specifically incorporated herein by reference and U.S. Pat. No. 3,240,780 "Amino-pyrazinoylguanidines", issued 3/15/66 to Cragoe et al., which is specifically incorporated herein by reference and other methods known or readily apparent to those skilled in the art. 3,4-dimethoxybenzamil can be synthesized according to the above U.S. Pat. Nos. 3,527,758 and 3,240,780 using the starting materials 3,4-dimethoxybenzylamine and 2-methyl-2-thiosendourea. These two compounds are reacted together to form an dimethoxybenzylguanidino intermediate. This intermediate compound is then reacted with methyl-3,5-diamino-6-chloropyrazine carboxylate to form 3,4-dimethoxybenzamil.

The compounds useful in the practice of this invention may be administered to mammals and neurons in dosages and dosage regimens sufficient to suppress hyperexcitability of the neurons. Although clinical trials have not been carried out, it is believed that dosages ranging from approximately 0.1 to 10 milligrams per kilogram body weight per day (mg/kg/day) will be preferred. Preferred dosages of amiloride are within the range of 1 to 5 mg/kg/day. Preferred dosages of benzamil and dimethoxybenzamil are within the range of 0.1 and 0.5 mg/kg/day. The compounds suitable for use in the invention may be administered in any convenient manner, such as intravenously, orally, or parenterally. The compounds may be formulated for oral administration in the form of capsules, tablets or the like.

Amiloride is a pyrazine ring compound clinically used in humans as a diuretic. Amiloride is a weak diuretic when administered alone and is presently used only in combination with HCTZ for its potassium sparing properties. The primary mechanism for its diuretic action is the blockade of a tetrodotoxin (TTX) insensitive sodium transport process in the kidney. TTX is a toxin that specifically blocks the voltage-sensitive sodium channel.

There have been few reports of studies of amiloride and its derivatives relating to calcium channel blocking activity. Pousti and Khoyi (Arach. int. Pharmacodyn. 242: 222-229, (1979) found that amiloride decreased the frequency of contractions of the spontaneously beating right atrium. Yamashita et al (J. of cardiovascular Pharm. 3: 704-7, (1981) found that amiloride had a negative chronotropic action on the SA node. These latter two studies did not recognize any calcium channel blocking activity of amiloride but the results are consistent with calcium channel blockade.

More recently, Bielefels and Hume (Circulation, Vol. 74, Abstract #686,1986) found one of the amiloride derivative, 3,4-dichlorobenzamil inhibited calcium currents in frog atrial cells. Garcia et al (Biophysical J. Vol. 51, p. 428a, 1987) found some derivatives of amiloride (guanidino-nitrogen and 5 amino-pyrazine nitrogen derivatives) inhibited calcium channel blocker binding to receptors of cardiac sarcolemmal membrane vesicles. These latter two studies recognized that some of the amiloride derivatives may have calcium channel blocking ability, but did not recognize the selective action on the T type calcium channel. No previous investigators have shown amiloride or its derivatives to possess a calcium channel blocking action selective for the T type channel. Nor have previous investigators shown that this group of compounds to have action on the calcium channels of neurons.

EFFECT OF AMILORIDE AND AMILORIDE DERIVATIVES ON NEUROBLASTOMA CELLS AND CHICK DORSAL ROOT GANGLION NEURONS

Experiments were performed on cultured neuroblastoma cells and chick dorsal root ganglion cells. Neuroblastoma cells from the cell line, N1E-115 were used. These cells were derived from cell lines of neurons from mouse adrenal glands. (Amano et al., "Neurotransmitter Synthesis By Neuroblastoma Clones." *Proc. Nat. Acad. Sci. U.S.A.* 69: 258-263, 1972). These neuroblastoma cells exhibited properties characteristics of differentiated neurons, such as neurotransmitter synthesis, axon formation, and possess the typical voltages activated sodium potassium and calcium channels. The cells were grown in petri dishes in DMEM (Dulbecco's Minimum Essential Medium, Sigma Chemical Co.) with 10 percent fetal bovine serum and 10 percent carbon dioxide. Dorsal root ganglion neurons were prepared from the dorsal root ganglion of 10 day-old chick embryos (gallus domesticus) and were cultured for 1 to 2 days prior to use in experiments following the procedure of Barde et al. "Sensory neurons in culture" *PNAS U.S.A.* 77:1199-1203.

The patch clamp technique described by Hamill et al was used in these studies. ("Improved patch-clamp techniques for high-resolution current recording from cells and cell-free membrane patches," *Pfluger Arch.*, 391:85-100, 1981.) This technique makes possible the precise measurement of current generate by ion flux through ion channels of small cells in response to a step change in membrane potential (voltage clamp). This technique also permits the precise measurement of the membrane potential while controlling the current stimulus (current clamp). Although described fully in the reference by Hamill et al, the basic procedure involves placing a fine glass pipette with a tip opening approximately 1-2 microns against the membrane of the cell to be studied. A gentle negative pressure is then applied to the fluid filled pipette opening. Next, a stronger negative pressure is applied to the inside of the pipette so that the cell membrane within the pipette opening ruptures. Thus, the inside of the cell becomes continuous with the inside of the pipette. The inside of the pipette is connected by a fine silver wire to a "patch clamp" amplifier that not only measures the small electric current generated by the cell, but also precisely controls the cell's membrane potential. The patch clamp technique thus makes possible the ability to control the important chemical an electrical parameter of the cell and measure the electric behavior of small individual cells.

In experiments where the measured currents is to reflect only current flowing through calcium channels, tetrodotoxin (TTX) was added to block the sodium channel. Potassium was completely replaced by cesium (Cs) and tetraethylammonium (TEA) to eliminate current through potassium channels. In these latter experiments the internal pipette solution consisted of 80 mM CsCl, 20 mM NaCl, 20 mM TEACl (tetraethylammonium chloride), 20 mM HEPES buffer (Sigma Chemical Co.), 10 mM EGTA (ethyleneglycoltetraacetic acid, Sigma Chemical Co.), 2 mM MgATP (adenosine triphosphate), 0.2 mM cAMP (cyclic adenosine monophosphate) and was titrated to pH 7.3. In general, the external solution consisted of 140 mM NaCl, 5 mM CaCl₂ 2 uM TTX, and 10 mM HEPES buffered to pH 7.3.

In current clamp experiments, the sodium and potassium currents were not eliminated. In these experiments TTX was not added to the external solution and cesium and TEA were replaced by potassium. The test compositions were added to the external solution.

SELECTIVE SUPPRESSION OF THE T TYPE CALCIUM CHANNEL IN NEUROBLASTOMA CELLS BY AMILORIDE

Figure 1A:
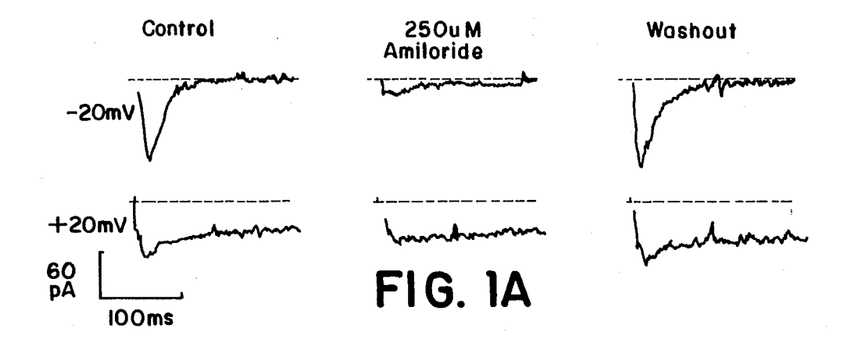
FIGS. 1A-D are graphs of the effects of amiloride on the T and L type calcium channels in neuroblastoma cells.
Figure 1B:
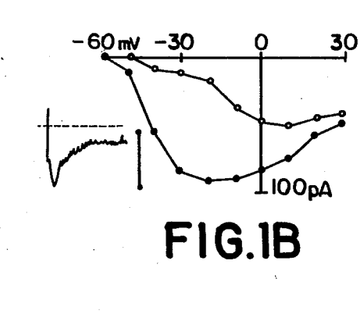
Figure 1C:
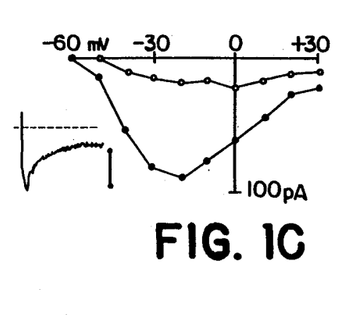
Figure 1D:
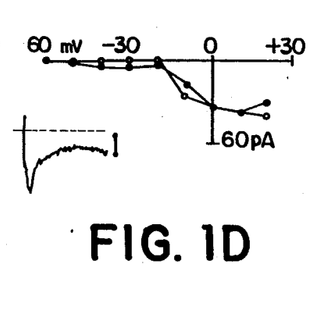

Two types of calcium channel currents can be measured in the neuroblastoma cell under voltage clamp conditions and under conditions where other channel currents are minimized. In FIG. 1A the calcium current through the T type calcium channel can be best seen upon depolarization to −20 mV (top trace). The current through the L type calcium channel can be best seen (second row of traces) upon depolarization to +20 mV. The membrane potential of the cell was held at −90 mV at rest. At that potential there is no measurable calcium current (dotted line being zero current). Upon rapid change of the membrane potential via the patch clamp amplifier to −20 mV a transient inward (downward deflection) current is activated followed by inactivation (return to baseline). This T type calcium channel current is characterized by its activation with weak depolarization and by its transient nature. Amiloride suppresses this T type channel current. On the other hand the L type is characterized by its activation with stronger depolarization and by its slow inactivation. Amiloride does not appreciably suppress this L type channel current. FIG. 1B, 1C, and 1D plot the total current, the transient current, and the slow inactivating current as a function of membrane potential. FIG. 1C again illustrates that amiloride (open circles) suppresses the transient current relative to control (filled circles). FIG. 1D illustrates that amiloride does not suppress the slow inactivating current.

SELECTIVE SUPPRESSION OF THE T TYPE CALCIUM CHANNEL IN DORAL ROOT GANGLION (DRG) NEURONS

Figure 2A:
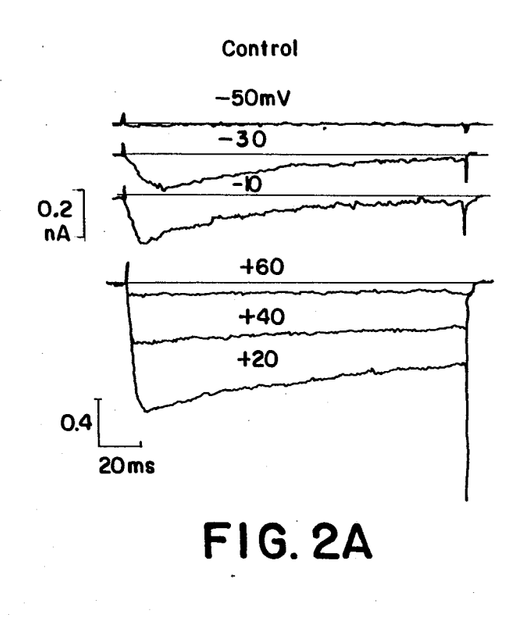
FIGS. 2A-B are graphs of the effects of amiloride on the L and T type calcium channels in chick dorsal root ganglion cells.
Figure 2B:
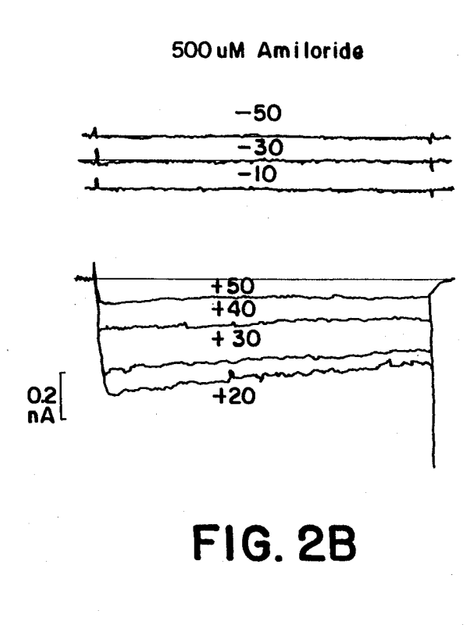

FIG. 2 illustrates voltage clamp experiments on DRG neurons. FIG. 2A shows that DRG neurons have both the T type calcium channel current (upper set of traces) and the L type current (lower set of traces). Amiloride completely suppressed the T type calcium channel current (FIG. 2B).

Figure 3:
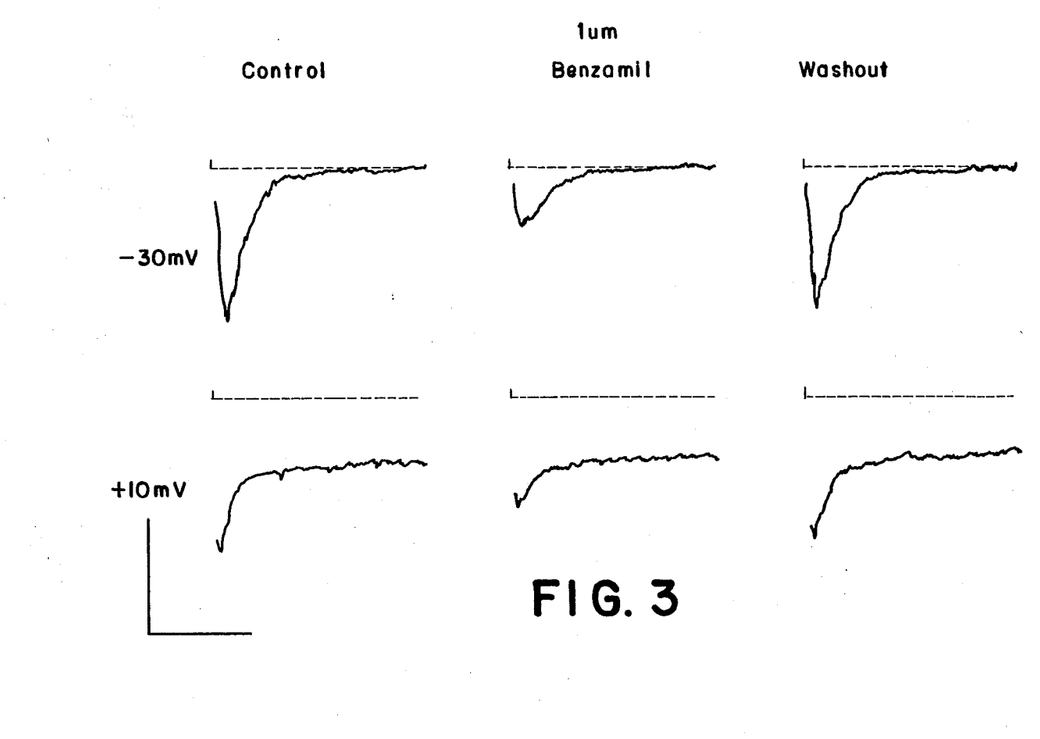
FIG. 3 is a graph of the effects of benzamil on the T and L type calcium channels in neuroblastoma cells.

Addition of a substituted benzyl moiety to a guanidino nitrogen greatly increases the potency of T type calcium channel suppression. FIG. 3 shows that 1 uM of benzamil reversably suppresses the bulk of the T type calcium channel current without suppressing the L type current. Dimethoxybenzamil similarly suppresses the T type current at this concentration. The addition of a benzyl moiety to the guanidine portion of the amiloride molecule increases the T channel activity by about fifty fold.

CONTRIBUTION OF THE T TYPE CALCIUM CHANNEL TO NEURONAL EXCITABILITY

Figure 4:
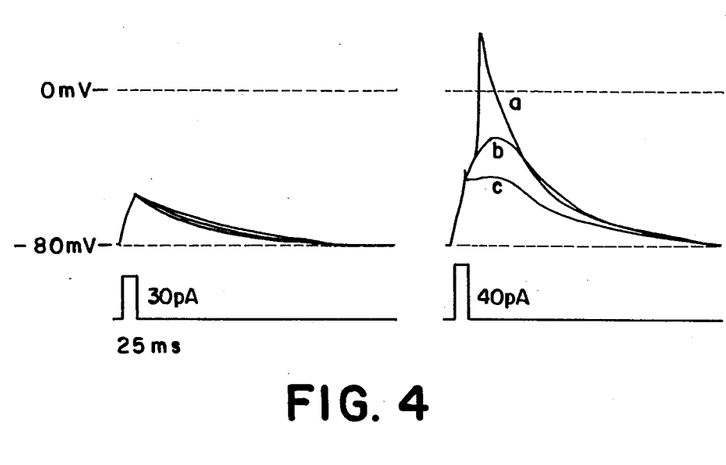
FIG. 4 is a graph of the effects of benzamil on the membrane potential of a neuroblastoma cell.
Figure 5:
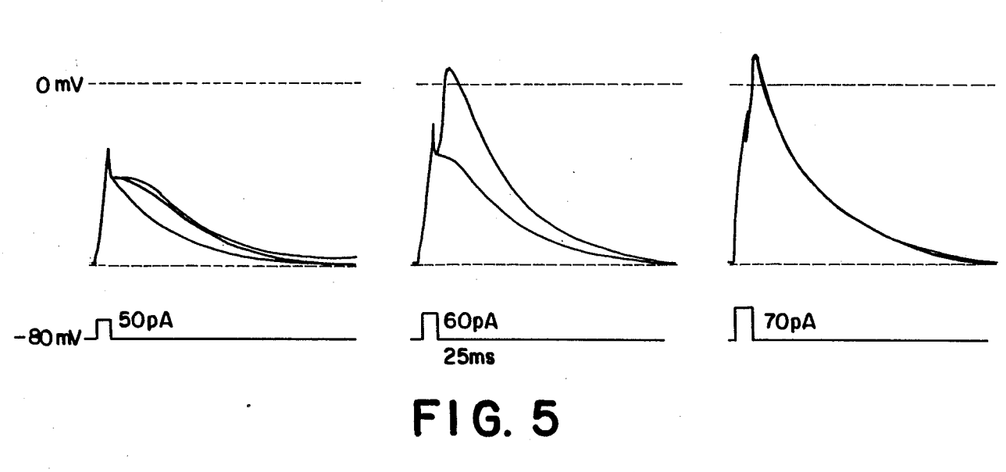
FIG. 5 is a graph of the effects amiloride on the membrane potential of a neuroblastoma cell.

FIGS. 4 and 5 show results of experiments conducted under current clamp conditions. In these experiments, the membrane potential was measured instead of the membrane current. In FIG. 4 (left traces) current pulses of 30 picoamps caused subthreshold membrane depolarization. On the right panel of FIG. 4, current pulses of 40 picoamps led to a regenerative depolarization spike similar to that of an action potential (trace a). Addition of 1 uM of TTX abolished the sodium component leaving only the contribution by calcium channel (traces b). Addition of 5 uM of benzamil, which selectively suppresses the current contributed by the T type calcium channel, further decreased the regenerative depolarization. Thus, we show that the T type calcium channel makes a significant contribution to neuronal excitability because it decreases the tendency for the cell to depolarize.

Further evidence that the T type calcium channel contributes to neuronal excitability is illustrated by FIG. 5. In FIG. 5 a current pulse is applied sufficient to bring the membrane potential to threshold (left most traces), to slightly about threshold (middle traces), and to well above threshold (right traces). At each degree of current stimulus the potential was recorded before, during, and after application of 250 uM of amiloride. It can be seen that selective suppression of the T calcium channel suppress neuronal excitability at membrane potential near the threshold for regenerative depolarization (the left and middle traces) but does not block the depolarization at higher degree of stimulation. Thus, suppression of the T type calcium channel by amiloride and its derivatives raises the threshold for neuronal excitation.

What is claimed is:

1. A method of regulating the excitability of neurons in a mammal comprising:
   administering to said mammal a substituted pyrazinoylguanidine having the formula wherein R is halogen; and R₁ is hydrogen, $C_1$–$C_4$ alkyl, benzyl or substituted benzyl; said substituted pyrazinoylguanidine being administered to said mammal in an amount sufficient to effect said regulation.

2. The method of claim 1 wherein the regulation of excitability is achieved through regulation of influx of calcium ions into the neurons.

3. The method of claim 2 wherein the regulation of influx is of influx of calcium ions through the T type calcium channel.

4. The method of claim 1 wherein administration of said substituted pyrazinoylguanidine is effected by administering said substituted pyrazinoylguanidine to a mammal at a dosage of from about 0.1 mg/kg/day to 10 mg/kg/day.

5. The method of claim 1 wherein R is chlorine, bromine or iodine.

6. The method of claim 1 wherein R₁ is hydrogen.

7. The method of claim 1 wherein R₁ is benzyl.

8. The method of claim 1 wherein R₁ is 3,4-dimethoxybenzyl.

9. The method of claim 1 wherein R₁ is $C_1$–$C_4$ alkyl.

10. The method of claim 1 wherein said substituted pyrazinoylguanidine is amiloride.

11. The method of claim 1 wherein said substituted pyrazinolyguanidine is benzamil.

12. The method of claim 1 wherein said substituted pyrazinolyguanidine is 3,4-dimethoxybenzamil.

13. The method of claim 1 wherein said substituted pyrazinoylguanidine is 6-bromoamiloride.

14. The method of claim 1 wherein said substituted pyrazinolyguanidine is 6-iodoamiloride.

15. A method of treating mammalian diseases characterized by hyperexcitability of neurons of a mammal comprising
administering to said mammal an amount of a substituted pyrazinoylguanidine effective to regulate the excitability of said neurons, said substituted pyrazinoylguanidine having the formula wherein R is halogen; and $R_1$ is a hydrogen, $C_1$-$C_4$ alkyl, benzyl or substituted benzyl.

16. The method of claim 15 wherein the regulation of excitability is achieved through regulation of influx of calcium ions into the neurons.

17. The method of claim 16 wherein the regulation of influx is of influx of calcium ions through the T type calcium channel.

18. The method of claim 15 wherein the substituted pyrazinoylguanidine is administered to the mammal at a dosage of from about 0.1 mg/kg/day to 10 mg/kg/day.

19. The method of claim 15 wherein R is chlorine, bromine or iodine.

20. The method of claim 15 wherein $R_1$ is hydrogen.

21. The method of claim 15 wherein $R_1$ is benzyl.

22. The method of claim 15 wherein $R_1$ is 3,4-dimethoxybenzyl.

23. The method of claim 15 wherein $R_1$ is $C_1$-$C_4$ alkyl.

24. The method of claim 15 wherein said substituted pyrazinoylguanidine is amiloride.

25. The method of claim 15 wherein said substituted pyrazinolyguanidine is benzamil.

26. The method of claim 15 wherein said substituted pyrazinolyguanidine is 3,4-dimethoxybenzamil.

27. The method of claim 15 wherein said substituted pyrazinoylguanidine is 6-bromoamiloride.

28. The method of claim 15 wherein said substituted pyrazinolyguanidine is 6-iodoamiloride.

29. The method of claim 15 wherein said regulation of excitability effects treatment of epilepsy.

30. The method of claim 15 wherein said regulation of excitability effects treatment of painful neuropathy.

31. The method of claim 15 wherein said regulation of excitability effects treatment of a central pain syndrome.

32. A method of selectively suppressing the T type calcium channel in neurons of a mammal comprising:
administering to said mammal an amount of a substituted pyrazinoylguanidine in an amount of sufficient to effect suppression, said substituted pyrazinoylguanidine having the formula wherein R is halogen; and $R_1$ is hydrogen, $C_1$-$C_4$ alkyl, benzyl or substituted benzyl.

33. The method of claim 32 wherein suppression is effected by administering the substituted pyrazinoylguanidine to the mammal at a dosage of from about 0.1 mg/kg/day to 10 mg/kg/day.

34. The method of claim 32 wherein R is chlorine, bromine or iodine.

35. The method of claim 32 wherein $R_1$ is hydrogen.

36. The method of claim 32 wherein $R_1$ is benzyl.

37. The method of claim 32 wherein $R_1$ is 3,4-dimethoxybenzyl.

38. The method of claim 32 wherein $R_1$ is $C_1$-$C_4$ alkyl.

39. The method of claim 32 wherein said substituted pyrazinoylguanidine is amiloride.

40. The method of claim 32 wherein said substituted pyrazinolyguanidine is benzamil.

41. The method of claim 32 wherein said substituted pyrazinolyguanidine is 3,4-dimethoxybenzamil.

42. The method of claim 32 wherein said substituted pyrazinoylguanidine is 6-bromoamiloride.

43. The method of claim 32 wherein said substituted pyrazinolyguanidine is 6-iodoamiloride.

44. The use in the manufacture of a medicament for treating a mammalian disease characterized by hyperexcitability of neurons of an affected mammal of a composition having the formula wherein R is halogen; and $R_1$ is hydrogen, $C_1$-$C_4$ alkyl, benzyl or substituted benzyl.

45. The use of claim 44 wherein said disease is epilepsy.

46. The use of claim 44 wherein said disease is painful neuropathy.

47. The use of claim 44 wherein said disease is a central pain syndrome.

48. The composition of claim 44 wherein R is chlorine, bromine or iodine.

49. The composition of claim 44 wherein $R_1$ is hydrogen.

50. The composition of claim 44 wherein $R_1$ is benzyl.

51. The composition of claim 44 wherein $R_1$ is 3,4-dimethoxybenzyl.

52. The composition of claim 44 wherein $R_1$ is $C_1$-$C_4$ alkyl.

53. The composition of claim 44 wherein said substituted pyrazinoylguanidine is amiloride.

54. The composition of claim 44 wherein said substituted pyrazinolyguanidine is benzamil.

55. The composition of claim 44 wherein said substituted pyrazinolyguanidine is 3,4-dimethoxybenzamil.

56. The composition of claim 44 wherein said substituted pyrazinoylguanidine is 6-bromoamiloride.

57. The composition of claim 44 wherein said substituted pyrazinolyguanidine is 6-iodoamiloride.

58. A composition of matter having the formula

* * * * *